United States Patent [19]

Cherpeck

[11] Patent Number: 5,300,701
[45] Date of Patent: Apr. 5, 1994

[54] PROCESS FOR THE PREPARATION OF POLYISOBUTYL HYDROXYAROMATICS

[75] Inventor: Richard E. Cherpeck, Cotati, Calif.

[73] Assignee: Chevron Research and Technology Company, San Francisco, Calif.

[21] Appl. No.: 997,982

[22] Filed: Dec. 28, 1992

[51] Int. Cl.$^5$ ............................................. C07C 37/00
[52] U.S. Cl. .................................. 568/792; 528/392; 568/790; 568/793
[58] Field of Search ............... 528/364, 392; 568/790, 568/792, 793

[56] References Cited

U.S. PATENT DOCUMENTS

| 3,849,085 | 11/1974 | Kreuz et al. | 44/78 |
| 4,231,759 | 11/1980 | Udelhofen et al. | 44/75 |
| 4,238,628 | 12/1980 | Cahill et al. | 568/736 |
| 5,175,225 | 12/1992 | Ruhe, Jr. | 526/272 |
| 5,192,335 | 3/1993 | Cherpeck | 44/387 |

FOREIGN PATENT DOCUMENTS 1159368  7/1969  United Kingdom .

Primary Examiner—John Kight, III
Assistant Examiner—Shelley A. Dodson
Attorney, Agent, or Firm—C. J. Caroli

[57] ABSTRACT

A process for the preparation of a polyisobutyl hydroxyaromatic compound which comprises alkylating a hydroxyaromatic compound in the presence of an acidic alkylation catalyst with a polyisobutene having a number average molecular weight in the range of about 300 to 5,000 and wherein the polyisobutene contains at least about 70% of a methylvinylidene isomer.

14 Claims, No Drawings

PROCESS FOR THE PREPARATION OF POLYISOBUTYL HYDROXYAROMATICS

BACKGROUND OF THE INVENTION

This invention relates to a process for the preparation of polyisobutyl hydroxyaromatics. More particularly, this invention relates to a process for the preparation of polyisobutyl hydroxyaromatics which comprises alkylating a hydroxyaromatic compound with a polyisobutene having a methylvinylidene isomer content of at least about 70%.

Alkylation of hydroxyaromatic compounds with polymeric olefins using acidic catalysts to generate alkylphenols is well known in the art. However, use of the acidic catalysts required for the alkylation reaction gives rise to concurrent polymer degradation and fragmentation of the polymeric alkyl substituent on the hydroxyaromatic compound. Known acidic alkylation catalysts have various fragmenting effects depending on the size of the alkylating agent. Most catalysts have little effect on olefin alkylating agents of up to about 20 carbon atoms, that is, having a number average molecular weight of up to about 280, but severe fragmentation occurs where alkylating agents of higher molecular weights are used. Polymeric alkylating agents are usually derived from propylene or butene and those comprised primarily of polybutene are the most susceptible to fragmentation during the alkylation reaction. When polybutenes having a number average molecular weight of 300 or greater are used, molecular weight degradation of either the olefin polymer or the substituted alkyl group occurs.

British Patent No. 1,159,368 disclosed that fragmentation of both the alkylating agent and alkyl substituent can be reduced but not eliminated by the use of certain specified reaction conditions. These conditions include the use of boron trifluoride-phenolate as the acidic catalyst and a temperature range of 0° C. to 65° C., with 0.1 to 1.1 moles of boron trifluoride and 1 to 4 moles of phenol per mole of mono-olefinic polymeric alkylating agent having a molecular weight of 700 to 300,000. Under these conditions, the fragmentation of polybutene can still only be restricted at best to a level of about a 10% reduction of average molecular weight.

U.S. Pat. No. 4,238,628 to Cahill et al. discloses a process to reduce the molecular weight degradation during the alkylation of benzene, phenol and naphthol which comprises alkylating the aromatic compound in the presence of a boron trifluoride catalyst with a $C_3$ or higher olefin polymer having terminal ethylene units.

According to the Cahill et al. process, the olefin polymer, preferably polybutene, is first reacted with ethylene to provide a polymer having terminal ethylene units. The polymer having such terminal ethylene units is then reacted with the aromatic compound under alkylating conditions. Cahill et al. teach that the olefin structure of the starting polybutene is predominantly the trisubstituted type with only minor amounts of vinylidene and terminal vinyl structures present.

Cahill et al. further teach that polyalkylphenols prepared with the use of polybutene without terminal ethylene units undergo molecular weight degradation due to the concurrent depolymerization reaction. Although the process disclosed in Cahill et al. results in a reduction in polymer degradation, the yield of the desired alkylaromatic product is not enhanced. In fact, the yield of alkylphenol reported by Cahill et al. ranged from about 44% to 64%.

Accordingly, there exists a need in the art for a hydroxyaromatic alkylation process which minimizes or eliminates molecular weight degradation while maintaining a high yield of the desired alkylaromatic product.

SUMMARY OF THE INVENTION

The present invention provides a novel process for the preparation of a polyisobutyl hydroxyaromatic compound which comprises alkylating a hydroxyaromatic compound in the presence of an acidic alkylation catalyst with a polyisobutene having a number average molecular weight in the range of about 300 to 5,000 and wherein the polyisobutene contains at least about 70% of a methylvinylidene isomer.

Among other factors, the present invention is based on the surprising discovery that hydroxyaromatic compounds can be effectively alkylated with a high molecular weight polyisobutene under acid-catalyzed reaction conditions in significantly high yield, while minimizing or substantially eliminating molecular weight degradation of the starting polyisobutene and the resulting polyisobutyl hydroxyaromatic, by employing a polyisobutene which contains a methylvinylidene isomer content of at least about 70%. Moreover, when the hydroxyaromatic compound is phenol, the resulting polyisobutyl phenol exhibits a high degree of para substitution, particularly when compared to alkylphenols prepared from conventional polybutenes having a low methyl vinylidene content.

DETAILED DESCRIPTION OF THE INVENTION

As noted above, the present invention provides polyisobutyl hydroxyaromatic compounds by a process which comprises alkylating a hydroxyaromatic compound in the presence of an acidic alkylation catalyst with a polyisobutene having a number average molecular of about 300 to 5,000 and a methylvinylidene isomer content of at least about 70%.

In general, the polyisobutyl substituent on the polyisobutyl hydroxyaromatic compound will have a number average molecular weight in the range of about 300 to 5,000, preferably in the range of about 400 to 3,000, and more preferably in the range of about 500 to 2,000.

The hydroxyaromatic compounds which may be alkylated in accordance with the process of the present invention include mononuclear monohydroxy and polyhydroxy aromatic hydrocarbons having 1 to 4, and preferably 1 to 3, hydroxy groups. Suitable hydroxyaromatic compounds include phenol, catechol, resorcinol, hydroquinone, pyrogallol, and the like. The preferred hydroxyaromatic compound is phenol.

The polyisobutene employed in the process of the present invention is a polyisobutene having a high methylvinylidene isomer content, that is, at least about 70% methylvinylidene Suitable high methylvinylidene polyisobutenes include those prepared using boron trifluoride catalysts. The preparation of such polyisobutenes in which the methylvinylidene isomer comprises a high percentage of the total olefin composition is described in U.S. Pat. Nos. 4,152,499 and 4,605,808, the disclosures of each of which are incorporated herein by reference.

The polyisobutene contemplated for use in the present invention will have a number average molecular weight in the range of about 300 to 5,000, preferably in the range of about 400 to 3,000, and more preferably in the range of about 500 to 2,000.

Examples of suitable polyisobutenes having a high methylvinylidene content include Ultravis 10, a polyisobutene having a molecular weight of about 950 and a methylvinylidene content of about 76%, and Ultravis 30, a polyisobutene having a molecular weight of about 1300 and a methylvinylidene content of about 74%, both available from British Petroleum.

The catalyst employed in the process of the present invention will generally be any of the well known acidic alkylation catalysts. Typical acidic alkylation catalysts include Lewis acids, trifluoromethanesulfonic acid, and acidic molecular sieve catalysts. Suitable Lewis acids include aluminum trichloride, boron trifluoride and boron trifluoride complexes, such as boron trifluoride etherate, boron trifluoride-phenol and boron trifluoride-phosphoric acid. Typical molecular sieve type catalysts include Amberlyst 36, available from Rohm and Haas, Philadelphia, Pa. Preferred acidic alkylation catalysts include trifluoromethanesulfonic acid, boron trifluoride and boron trifluoride complexes. In general, the stronger acidic alkylation catalysts will be employed with higher molecular weight polyisobutenes.

Typically, the reaction temperature for the alkylation reaction will be in the range of about 0° C. to 100° C., and preferably in the range of about 20° C. to 60° C. The reaction pressure will generally be atmospheric, although higher or lower pressures may be employed.

The molar ratio of the hydroxyaromatic compound to polyisobutene is normally in the range of about 1.2:1 to 5:1, and preferably will be in the range of about 2:1 to 3:1. In general, the number of equivalents of the acidic alkylation catalyst per equivalent of polyisobutene will be in the range of about 0.005:1 to 5:1, and preferably in the range of about 0.05:1 to 0.6:1.

The alkylation reaction may be carried out neat or in the presence of a solvent which in inert to the reaction of the hydroxyaromatic compound and the polyisobutene. When employed, a typical solvent is hexane.

The alkylation reaction will generally be carried out over a period of about 2 to 48 hours, and preferably over a period of about 3 to 20 hours. Upon completion of the reaction, the desired polyisobutyl hydroxyaromatic compound is isolated using conventional techniques.

The following examples are presented to illustrate specific embodiments of this invention and are not to be construed in any way as limiting the scope of the invention.

EXAMPLES

Example 1

Preparation of Polyisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 milliliters of boron trifluoride etherate was added dropwise. 1040 grams of Ultravis 10 polyisobutene (molecular weight 950, 76% methylvinylidene, available from British Petroleum) was dissolved in 1,863 milliliters of hexane. The polyisobutene was added to the reaction at a rate to maintain the temperature between 22°-27° C. The reaction mixture was stirred for 16 hours at room temperature. Then, 400 milliliters of concentrated ammonium hydroxide was added followed by 2,000 milliliters of hexane. The reaction mixture was washed with water (3×2,000 milliliters), dried over magnesium sulfate, filtered and the solvents removed under vacuum to yield 1,056.5 grams of a crude reaction product. The crude reaction product was determined to contain 80% of the desired product by proton NMR and chromatography on silica gel eluting with hexane, followed by hexane; ethylacetate: ethanol (93:5;2).

Example 2

Various alkylation reactions were carried out in accordance with the process of the present invention, using polyisobutenes having a high methylvinylidene isomer content. These reactions were compared with alkylation reactions employing conventional polyisobutenes having only minor amounts of methylvinylidene isomer present.

The polyisobutenes employed in the alkylation reactions demonstrating the present invention were Ultravis 10 polybutene having a number average molecular weight of about 950 and a methylvinylidene isomer content of about 76% and Ultravis 30 polyisobutene having a number average molecular weight of about 1300 and a methylvinylidene isomer content of about 74%, both of which are commercially available from British Petroleum. The polyisobutenes employed for comparison purposes were Parapol 950 polyisobutene having a number average molecular weight of about 950 and a methylvinylidene isomer content of about 2% and Parapol 1300 polyisobutene having a number average molecular weight of about 1300 and a methylvinylidene isomer content of about 6%, both available from Exxon Chemical Company.

Each of the alkylation reactions were carried out using 2 equivalents of phenol as the hydroxyaromatic compound and 1 equivalent of polyisobutene. The reactions were carried out over a period of about 15 hours.

The results are shown in Table 1. These results show that the alkylation reactions of the present invention employing high methylvinylidene polyisobutene provided the desired polyisobutyl phenol in significantly higher yield than the alkylation reactions employing conventional polyisobutene having minor amounts of methylvinylidene. In addition, the polyisobutyl phenols prepared in accordance with the present invention exhibited minimal molecular weight degradation. Moreover, the polyisobutyl phenols produced pursuant to the present invention contained an average of about 70% to 100% para-substitution. This compares to an average of about 0% to 40% para-substitution for the polyisobutyl phenols prepared with the conventional low vinylidene polyisobutenes. Para-substituted polyisobutyl phenols are preferable for a number of uses. For example, when polyisobutyl phenols are employed as fuel additives, para-substitution generally provides enhanced fuel additive performance.

TABLE 1

| Run No. | Polyisobutene | Acidic Catalyst | Mole Equiv. (Catalyst) | Temperature. °C. | Yield | Mol. Wgt. (VPO)[a] | Mol. Wgt. (PMR)[b] |
|---|---|---|---|---|---|---|---|
| 1 | Parapol 950 | $CF_3SO_3H$ | .05 (0.8 wt. %) | Room Temp.[c] | 61% | 1069 | 1162 |
| 2 | Ultravis 10 | $CF_3SO_3H$ | .05 | Room Temp.[c] | 91% | 1114 | 1106 |
| 3 | Parapol 950 | $BF_3.Et_2O$ | .55 | Room Temp.[c] | 15% | 604 | 656 |
| 4 | Ultravis 10 | $BF_3.Et_2O$ | .55 | Room Temp.[c] | 80% | 1197 | 1218 |
| 5 | Parapol 950 | $BF_3.H_3PO_4$ | .55 | Room Temp.[c] | 11% | 533 | 600 |
| 6 | Ultravis 10 | $BF_3.H_3PO_4$ | .55 | Room Temp.[c] | 83% |  | 1162 |
| 7 | Parapol 950 | $BF_3$.phenol | .55 | Room Temp.[c] | 90% |  | 656 |
| 8 | Ultravis 10 | $BF_3$.phenol | .05 | 45° C.[d] | 82% |  | 994 |
| 9 | Parapol 1300 | $CF_3SO_3H$ | .05 | Room Temp.[c] | 14% | 1088 | 994 |
| 10 | Ultravis 30 | $CF_3SO_3H$ | .05 | Room Temp.[c] | 71% | 1521 | 1386 |

[a] VPO = vapor pressure osmometry
[b] PMR = proton magnetic resonance
[c] Room Temperature was approximately 23° C.
[d] Reaction time was 5 hours.

What is claimed is:

1. A process for the preparation of a polyisobutyl hydroxyaromatic compound which comprises alkylating a hydroxyaromatic compound in the presence of an acidic alkylation catalyst with a polyisobutene having a number average molecular weight in the range of about 300 to 5,000 and wherein the polyisobutene contains at least about 70% of a methylvinylidene isomer.

2. The process according to claim 1, wherein the hydroxyaromatic compound is phenol.

3. The process according to claim 1, wherein the polyisobutene has a number average molecular weight of about 400 to 3,000.

4. The process according to claim 3, wherein the polyisobutene has a number average molecular weight of about 500 to 2,000.

5. The process according to claim 1, wherein the acidic alkylation catalyst is selected from the group consisting of a Lewis acid, trifluoromethane sulfonic acid and an acidic molecular sieve.

6. The process according to claim 5, wherein the acidic alkylation catalyst is a Lewis acid.

7. The process according to claim 6, wherein the Lewis acid is boron trifluoride or a boron trifluoride complex.

8. The process according to claim 5, wherein the acidic alkylation catalyst is trifluoromethane sulfonic acid.

9. The process according to claim 1, wherein the alkylation temperature is in the range of about 0° to 100° C.

10. The process according to claim 9, wherein the alkylation temperature is in the range of about 20° to 0 60° C.

11. The process according to claim 1, wherein the molar ratio of hydroxyaromatic compound to polyisobutene is about 1.2:1 to 5:1.

12. The process according to claim 11, wherein the molar ratio of hydroxyaromatic compound to polyisobutene is about 2:1 to 3:1.

13. The process according to claim 1, wherein the number of equivalents of catalyst per equivalent of polyisobutene is about 0.005:1 to 5:1.

14. The process according to claim 13, wherein the number of equivalents of catalyst per equivalent of polyisobutene is about 0.05:1 to 0.6:1.

* * * * *